United States Patent [19]
Ridgeway

[11] Patent Number: 5,710,551
[45] Date of Patent: Jan. 20, 1998

[54] SELF-MEDICATION MONITORING SYSTEM

[76] Inventor: Donald G. Ridgeway, 1852 Blacks Rd., Hebron, Ohio 43025

[21] Appl. No.: 507,546

[22] Filed: Jul. 26, 1995

[51] Int. Cl.$^6$ .................................................. G08B 19/00
[52] U.S. Cl. .......................... 340/870.09; 340/309.15; 340/568; 364/479.01; 128/920; 221/15
[58] Field of Search .................. 340/870.09, 870.01, 340/870.16, 568, 309.15; 264/479.01, 569; 128/630, 920; 221/9, 15

[56] References Cited

U.S. PATENT DOCUMENTS

| | | | |
|---|---|---|---|
| 4,911,327 | 3/1990 | Shepherd et al. | 221/15 |
| 5,016,172 | 5/1991 | Dessertine | 128/920 |

OTHER PUBLICATIONS

"Management Overview of Significant Noncompliance Research Findings," Target Microsystems, 1997.

"Medi–Minder t" (tm) Product Brochure, Target Microsystems, Dec. 10, 1996.

"The New Urgency of Noncompliance Prevention," by Donald G. Ridgeway, Drug Topics, Mar. 3, 1997, pp. 24 & 26.

Two Product Brochures (4 pages Total) Describing the MED–Companion Medication Monitoring System, (Circa 1995).

*Primary Examiner*—Jeffrey Hofsass
*Assistant Examiner*—Andrew Hill

[57] ABSTRACT

A system for the remote monitoring of in-home self-medication to assure compliance with prescribed dosage schedules. The system comprises at least one subscriber home medication station which interfaces with a communications link and a remote central monitoring station also interfaced with the link and operative to receive and analyze messages transmitted by the home medication station. The preferred home medication station embodiment transmits messages to the central station over the communications link each time the home medication station is accessed for a dosage of medication. Central station computer means verify receipt of such signals within each subscriber's uniquely scheduled dosage time windows, and alert an operator to take appropriate action if a dosage schedule error is detected. Alternative home medication station embodiments utilize a built-in programmable timer module to verify accessing of medication within a subscriber's uniquely scheduled dosage time windows, and to initiate transmission of alarm signals to the central station over the communications link if dosage schedule errors are detected by the timer module. All embodiments provide subscribers with help-button means to initiate transmission of alarm messages to the central station over the communications link in event of adverse reaction to medication, or other emergencies. Since the central station will be alerted if any scheduled dosage is missed, no emergency rendering a subscriber unable to press a help-button or call for help can go undetected longer than the maximum time between consecutively scheduled dosages.

15 Claims, 8 Drawing Sheets

PREFERRED EMBODIMENT

FIGURE 3

LOAD/USE SWITCH WIRING

FIGURE 4

RECESS-MOUNTED LOAD/USE SWITCH

FIGURE 5

PROGRAMMABLE TIMER MODULE

ALTERNATIVE EMBODIMENT "A"

FIGURE 8

PORTABLE PROGRAMMING TERMINAL

SELF-MEDICATION MONITORING SYSTEM

BACKGROUND—FIELD OF INVENTION

This invention relates generally to medication monitoring, and more specifically to the remote monitoring of in-home self-medication to assure compliance with prescribed dosage schedules.

BACKGROUND—DESCRIPTION OF PRIOR ART

This invention provides a solution for what's often referred to as today's "other drug problem":

In America, about 125,000 persons die annually because they didn't take their medicine as prescribed . . . roughly twice the number of Americans killed annually in automobile accidents. 1

For people over 65, about 30% of hospital admissions are due to not taking medication as prescribed. 2

The inability to reliably self-medicate at home is the cause of about 40% of nursing home admissions. 3

Medication non-compliance is thus a serious problem, particularly for older Americans, and there are a great many. The 1990 Census counted 31.2 million Americans aged 65 or older, and their numbers are expected to increase to more than 70 million over the next 40 years. The Census also found that 1 in 4 persons aged 65 or older live alone, comprising 40% of all single-person households. Various surveys have further shown that the vast majority of elderly persons who live alone want to maintain an independent lifestyle as long as possible. Also, cost and availability of quality senior group-housing alternatives frequently mandates the prolonging of an independent lifestyle as a matter of economic necessity. A reliable method for monitoring self-medication will thus benefit literally millions of elderly persons by enabling them to enjoy living safely at home longer.

The need for effective self-medication monitoring solutions has been widely recognized, but has remained substantially unfilled. A recent patent search revealed no relevant prior art. A recent market survey identified only one system being marketed. The system, "MED-Companion", is billed as a "monitoring service with automated medication dispenser." As the only relevant prior art identified, MED-Companion necessarily serves as the focal point for the following brief critique of the state of the art.

MED-Companion allows a week's supply of medication to be loaded into a refillable plastic cassette which is then locked into a dispenser console. The console is programmable to dispense individual dosages into a drawer at prescribed dosage times, concurrently sounding a buzzer. If the medicine is not removed from the drawer within a pre-programmed time, an encoded alarm signal is telephoned to a remote monitoring center. Discussions with health care professionals revealed the following criticisms:

The Pavlovian operating concept, prompt response to a buzzer, will annoy many subscribers, and there's no real need for it. Most medication doesn't have to be taken at precise times, a bandwidth of +/− several minutes is normally acceptable.

The design doesn't include an effective means for a subscriber to signal the monitoring center in event of an adverse reaction to medication.

Its complicated appearance will intimidate many of the elderly, it looks like a piece of laboratory equipment.

Monthly lease cost, predicated by design complexity, is generally prohibitive.

MED-Companion reports by exception, the monitoring center hears from it only in event of a medication alarm. Equipment failure blocking message transmission would therefore look the same as 100% dosage compliance to the monitoring center, and wouldn't be automatically detected.

Neither does MED-Companion's sophistication provide 100% positive assurance that medication is actually taken. Its locked dispenser implies intended use by subscribers who can't be trusted to access proper dosage amounts. Yet its monitoring mechanism is satisfied if the dispensing drawer is opened and closed at a scheduled dosage time. But if removed from the drawer, was the dosage taken immediately? Was it taken at all?

In absence of positive feedback in the form of measured physiological response to medication, such as heart rate, blood pressure, or blood chemistry, no automated remote monitoring technique can provide 100% assurance that medication is actually taken. But such feedback would typically be costly, complex, inconvenient, and actually unnecessary for a majority of subscriber candidates. Most subscriber candidates can be regarded as forgetful but basically mentally competent, a large segment of the elderly population. A much smaller population segment, persons who can't be relied upon to take medication once in hand, should not be regarded as candidates for any automated monitoring technique.

Practicality therefore validates a monitoring methodology founded on the inference that medication will be both removed and taken when a monitored container is accessed. That being the case, simple container designs can be expected to maximize dosage schedule compliance as well or better than designs as complex as MED-Companion, and at a lower cost.

This invention advocates the monitoring of a simple container with a hinged or removable lid. Medication can be stored inside directly, or in boxes, bottles, or dispensers to suit user needs. A variety of switch types can be used to produce contact closure signals when the lid is opened and closed during removal of a dosage of medication. A range of simple container designs can be built very inexpensively, but more significantly, monitoring system development costs are minimal. A full range of hardware and software needed for the remote monitoring of contact closure signals is well known and widely used in monitored security systems which protect homes and businesses from fire and burglary.

In such security systems, alarm sensors at monitored sites typically produce contact closure signals, which cause an on-site digital communicator to responsively transmit digitally encoded alarm messages to a central monitoring station, usually by means of the interconnected telephone network. Central stations have extensive alarm monitoring capabilities, including means to monitor the opening and closing of businesses within specified windows of time. Such open/close monitoring capabilities are readily adaptable to monitoring medication containers to assure that medication is accessed within scheduled dosage time windows. Central stations also typically maintain computer databases which can contain comprehensive information on each monitored subscriber, including phone numbers for responders, police, fire department, ambulance service, and the like. Most such databases can also routinely include medically-related information paramedics might need if summoned to respond to a medical emergency.

All hardware/software system building blocks needed to comprise a system for monitoring in-home self-medication activities thus exist in pre-proven form. This invention basically integrates well known security system apparatus into the design of a medication container, and prescribes a method for adapting a typical security system central station to monitor in-home self-medication activities.

Development of this invention revealed that a number of security system manufacturers offer digital communicators suitable for incorporation into a medication container design. As a bonus feature, all digital communicators evaluated were also found to be capable of easily accommodating input signals from simple push-button switches, often referred to as "help-buttons". Such "help-button" protection could often be invaluable in alerting dispatchers to respond to adverse reactions to certain types of medication. There was also typically a capability to extend "help-button" protection to portable miniature wireless transmitters, and to automatically enable 2-way voice conversations between a central monitoring station and speakerphone capabilities at the monitored site under alarm conditions.

Accordingly, this invention can easily be optionally provided with all help-button and 2-way audio capabilities commonly found in state-of-the-art security systems. With or without such capabilities, however, this invention adds an important new dimension to monitoring protection. Subscriber well-being can be inferred as a by-product of indication that medication is being taken per schedule. Central station dispatchers will initiate follow-up procedures the first time a scheduled dosage of medication is missed, for whatever reason. The longest time any in-home emergency might go undetected is therefore the maximum time between consecutively scheduled dosages of medication.

Availability of this invention will therefore provide comprehensive protection and welcome peace of mind for literally millions of the elderly and infirm who want to live independently as long as possible. The threat of self-medication error hazards is effectively countered, and often of equal importance, there need be no fear of lying helpless for days as mishaps turn into tragedies.

References cited in the preceding paragraphs:

1 A. Anderson, Update on Patient Non-Compliance
2 Arch Intern Med 1990; 50:841–845
3 Feasibility Study, Biomedical Business International, 1/1988

OBJECTS AND ADVANTAGES

Accordingly, several objects and advantages of the present invention are:

(a) to provide a reliable in-home self-medication apparatus and method for remote monitoring to assure compliance with prescribed dosage schedules;

(b) to provide early detection of forgotten dosages and off-schedule accessing of medication so that adverse effects of such errors can be minimized;

(c) to provide a simple design with a low overall cost, in order to make the apparatus and monitoring affordable for a maximum number of elderly subscribers;

(d) to provide a design which is easy to use, non-intimidating, and non-demeaning to elderly subscribers;

(e) to provide subscribers with latitude to take medication within time windows of specifiable width, as opposed to requiring that medication be taken at specific times;

(f) to automatically provide frequent verification of proper operation of in-home communicator electronics;

(g) to automatically verify subscriber well-being as a byproduct of the monitoring of self-medication activities;

(h) to provide subscribers with effective means to alert the monitoring center if help is needed in event of an adverse reaction to medication.

These and other objects and advantages of the present invention will become apparent from a consideration of the ensuing description and drawings.

DRAWING FIGURES

This invention will be more fully understood by reference to the accompanying drawings, in which.

REFERENCE NUMBERS USED IN DRAWINGS 1 central monitoring station
2 subscriber home medication station
3 communications link
4 cylindrical proximity lid switch
5 cylindrical permanent magnet
6 help-button switch
7 false bottom
8 miniature portable help-button RF transmitter, optional
9 false bottom spacer blocks
10 1-channel RF receiver, optional
11 screw fasteners
12 digital communicator
13 ornamental box
14 programmable timer module
16 pill dispenser, recommended
17 2-way audio module, optional
18 load/use switch
19 spacer mounts, optional
20 load/use LED indicator
21 microphone, optional
22 AC adapter, converts AC to DC
24 DC power cord
25 switch mounting panel
26 terminal strip
28 communications cord
29 feed-through grommets
30 1-line modular plug
32 Y-connector splitter
34 backup battery 36 timer logic
38 keyboard
40 LCD display
42 reset switch
44 local annunciator
46 programming terminal
47 speaker, optional

DESCRIPTION—FIGS. 1 TO 8

In accordance with the present invention, a self-medication monitoring system is disclosed. A functional overview of the system is presented in FIG. 1. A home medication station 2 is typically located in the home of a subscriber. A lid switch 4 is actuated each time a dosage of medication is removed from the home medication station. A help-button 6 is a simple momentary push-button switch which a subscriber may press in event of an adverse reaction to medication. Upon actuation of switches 4 or 6, communicator logic within the home medication station becomes operative to transmit one or more messages to a central monitoring station 1 over a communications link 3.

Figure 1:
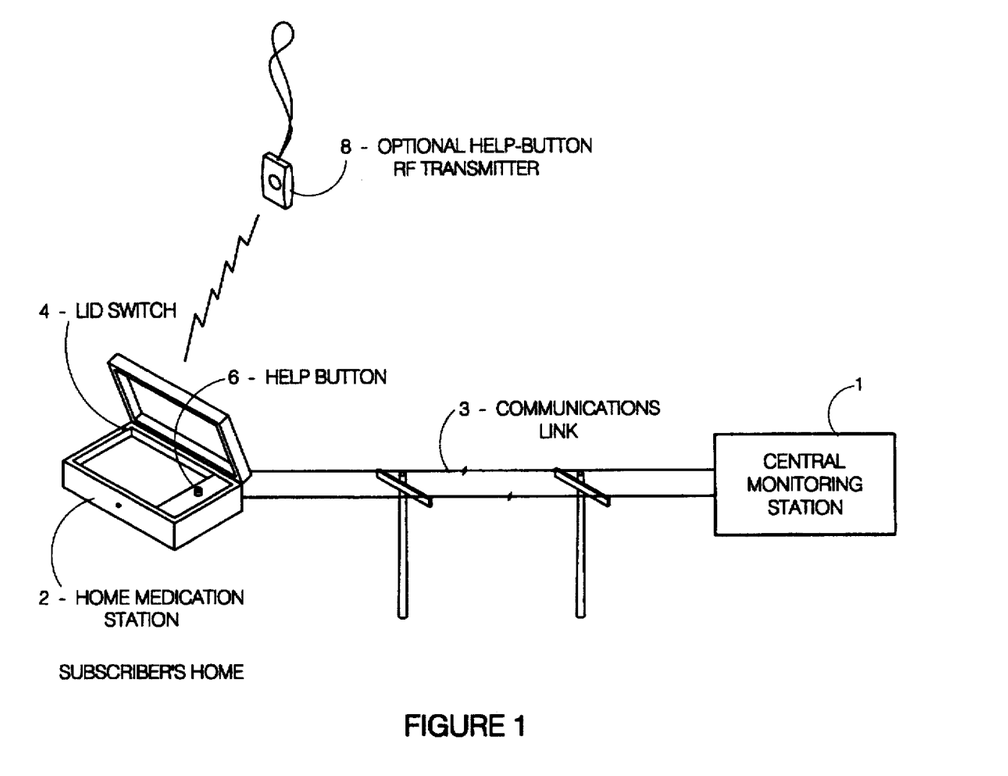
FIG. 1 is a functional system overview showing the communications link interface between a typical subscriber home medication station and a central monitoring station.

Communications link 3 is normally the interconnected telephone network, but may also comprise a satellite communications link, a cable television communications link, a radio frequency communications link, a directly wired communications link, or any other suitable media for transmission of messages from a subscriber's home to the central station.

In all embodiments of this invention, dispatchers at the central station are alerted if a dosage schedule error is detected. A dispatcher will telephone the subscriber, if possible, thereby prompting early correction of dosage errors. Dispatchers are also alerted if a subscriber actuates help-button 6, or an optional portable help-button RF transmitter 8. If a subscriber cannot be reached by phone, a responder is immediately dispatched to the subscriber's home to investigate.

A simple design and simple operating procedures are foundational in all embodiments. Home health care professionals polled during development of this invention observed that most subscribers will be elderly, and that most elderly persons are not comfortable in dealing with gadgetry or operational complexities. Also, reliable statistics indicate that a majority of subscribers will be elderly women, so attractive appearance was also regarded to be of importance.

Figure 2:
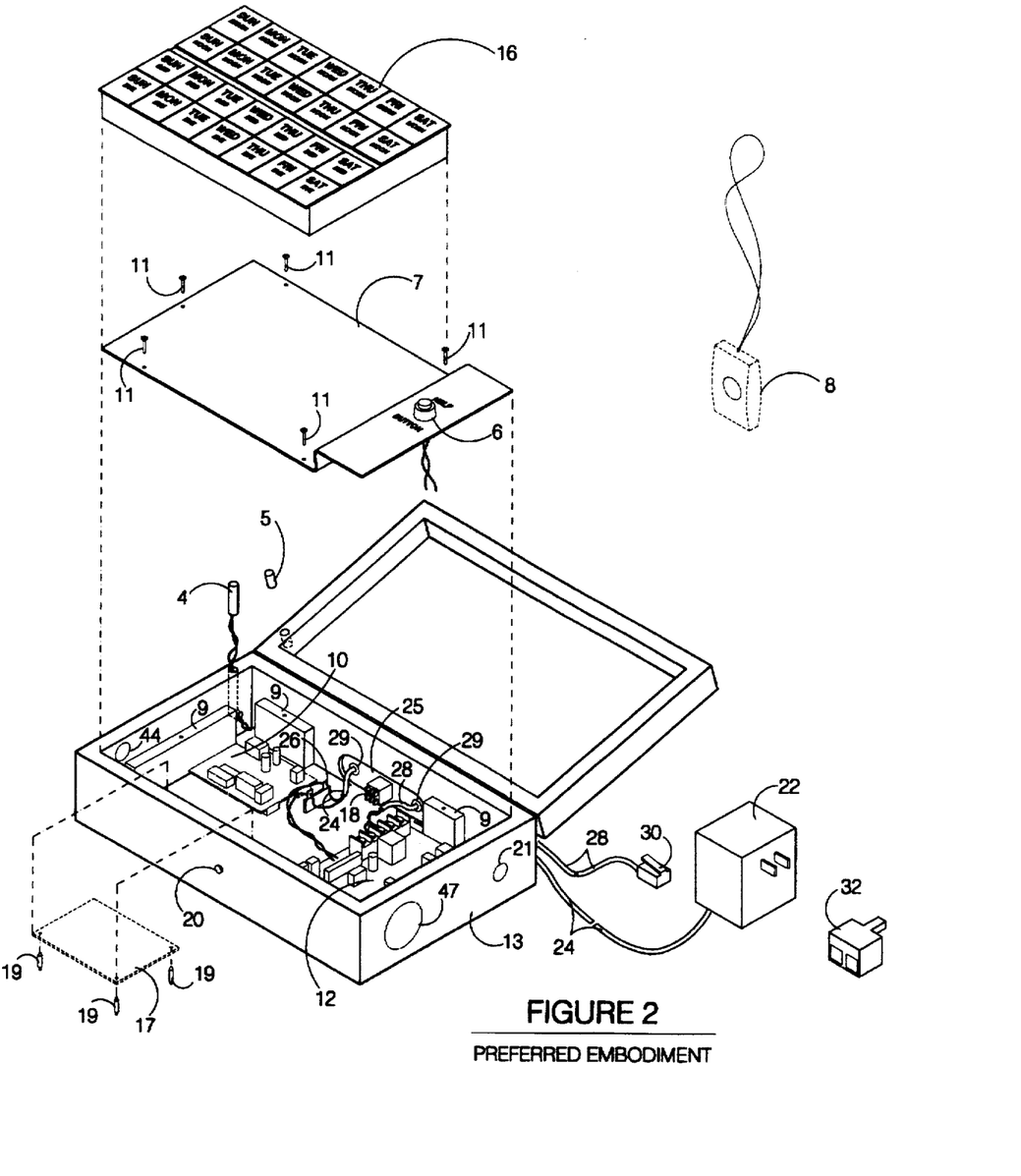
FIG. 2 is an exploded isometric view of the preferred embodiment of a subscriber home medication station.

FIG. 2 illustrates a general home medication station design concept which is proposed for all embodiments. Although a range of container designs could be used, it is recommended that all home medication station elements should be housed in a simple non-metallic ornamental box 13. Box 13's lid could be removable, but a hinged lid is regarded as easier to use for elderly hands. The proposed construction for box 13 is attractively finished wood or plastic, similar in appearance to a quality jewelry box.

A non-metallic false bottom 7 divides box 13 into an upper cavity and a lower cavity. False bottom 7 can be made from wood or plastic, thermo-formed ABS plastic works well. Spacer blocks 9 and screw fasteners 11 provide a good method for securing false bottom 7 to box 13. Non-metallic materials for box 13 and false bottom 7 allow radio signals from optional miniature help-button RF transmitter 8 to pass through and be received by optional RF receiver 10.

Overall dimensions of box 13 are selected to provide adequate space for the required contents of both cavities. The upper cavity contains medication, either stored directly or in dispensers best suited to meet subscriber needs. It can also contain preloaded tokens, to be removed in sequence to provide subscribers with a dosage compliance audit trail as scheduled injections of medication such as insulin are self-administered. Systematic token removal plus monitored self-medication can virtually eliminate the possibility of double-dosing due to subscriber uncertainty as to whether or not a shot has been self-administered, a major cause of medication-related diabetic fatalities.

In the great majority of cases, however, in-home medication is in pill or capsule form. The upper cavity should in that case be large enough to contain multi-compartment pill dispensers in popular use. FIG. 2 illustrates optional use of a multi-compartment pill dispenser 16 such as "Medi-Planner II" by Health Enterprises. Its external dimensions are roughly 8.3"×5.5"×1", and its 28 extra-large compartments allow it to be preloaded with up to 4 daily dosages for an entire week. Its clearly labeled see-through compartments also greatly aid subscribers in the self-pacing of dosage schedules. Such containers work well in token removal applications to keep track of self-injections, as well as for normal dosage preloads.

Box 13's lower cavity must in all cases be large enough to house the required electronic apparatus. All embodiments require sufficient space for a digital communicator 12. Space may also optionally be required for a 1-channel RF receiver 10, a 2-way audio module 17, and a programmable timer module 14 in alternative embodiments. All four of the preceding devices 10, 12, 14, and 17 are typically packaged on small PC boards.

Digital communicators are available as standalone products from a number of security system manufacturers, including C & K Systems, Linear Corporation, and Visonic Ltd. In security systems, digital communicators typically accept voltage signals generated by alarm sensor contact closures, and responsively transmit encoded alarm messages to central monitoring stations, usually via the interconnected telephone network. Encoded messages identify both monitored site location and the point number(s) assigned to the sensor(s) that signaled the alarm condition(s). Capacities of 4 or 8 input points are typical for small digital communicators best suited for this application.

Digital communicators sold as standalone products commonly have the ability to interface with 2-way audio modules, which in turn interface with miniature speakers and microphones. Such audio modules automatically enable 2-way conversation between central station dispatchers and no-hands speakerphone capabilities in subscriber homes during alarm conditions. Although rarely required in self-medication monitoring applications, such 2-way audio capabilities can be easily added to all embodiments of this invention. Miniature speakers and microphones are easily mounted in box 13's side walls, dashed lines in FIG. 2 show locations which have worked well.

RF receiver 10 is a small 1-channel unit equipped with an output relay which responsively applies a voltage signal to one of digital communicator 12's input points upon receipt of a radio signal from miniature portable help-button RF transmitter 8. Both receiver 10 and transmitter 8 can be obtained from suppliers such as Visonic Ltd.

FIG. 2 conceptually illustrates the preferred home medication station embodiment, dashed lines show recommended placement of major options. During development of this invention, a prototype home medication station model was built which included a digital communicator 12, a RF receiver 10, a 2-way audio module 17, a 1" diameter pm speaker 47, and a condenser microphone 21 measuring 0.29"

high×0.39" diameter. The mounting placement for these devices was essentially as shown in FIG. 2. The digital communicator 12 and the 1-channel RF receiver 10 were secured to the bottom of box 13 by adhesive backed hook & loop fastener strips. The 2-way audio module 17, a small PC board, was positioned above digital communicator 12 by spacer mounts 19. The prototype, which also included sufficient space for a "Medi-Planner II" pill dispenser 16, was housed in a wooden ornamental box 13 which had external dimensions of approximately 7"×4"×12".

In all embodiments, a lid switch 4 is actuated when box 13 is opened and closed during removal of a dosage of medication. Although a variety of switch types could be used, a cylindrical magnetic proximity switch 4 actuated by a cylindrical magnet 5 offer the benefits of economy, mounting ease, neatness, and reliability. Such switch/magnet pairs are commonly used in security systems to detect door or window opening movement. A normally-open switch design is standard, with switch contacts held in closed position by a magnet which pulls away with door/window movement, causing switch contacts to open. As shown in FIG. 2, switch 4 and magnet 5 can be flush-mounted in holes drilled in box 13's side panels. Switch wires feed into box 13's lower cavity through a hole drilled into a side panel which intersects the bottom of the hole which contains switch 4.

In the preferred embodiment, lid switch 4 directly actuates one of digital communicator 12's input points. In alternative embodiments, lid switch 4's contact closure signals are applied to programmable timer module 14. In all embodiments, a load/use switch 18 disables lid switch 4 so that box 13 can be opened to load in a supply of medication without signaling the central station.

A low-profile DPDT toggle switch is a good choice for load/use switch 18. When in the "Load" position, one SPDT side of load/use switch 18 closes in parallel with lid switch 4. As long as load/use switch 18 remains in the "Load" position, the opening of box 13 therefore cannot be sensed by digital communicator 12 in the preferred embodiment, or by programmable timer module 14 in alternative embodiments. The other SPDT side of load/use switch 18 concurrently energizes a blinking red LED indicator 20, flush-mounted in the front of box 13. LED indicator 20 provides visual confirmation that lid switch 4 is disabled, and continues to blink brightly as a reminder that load/use switch 18 must be returned to "Use" position after a supply of medication has been loaded.

Figure 3:
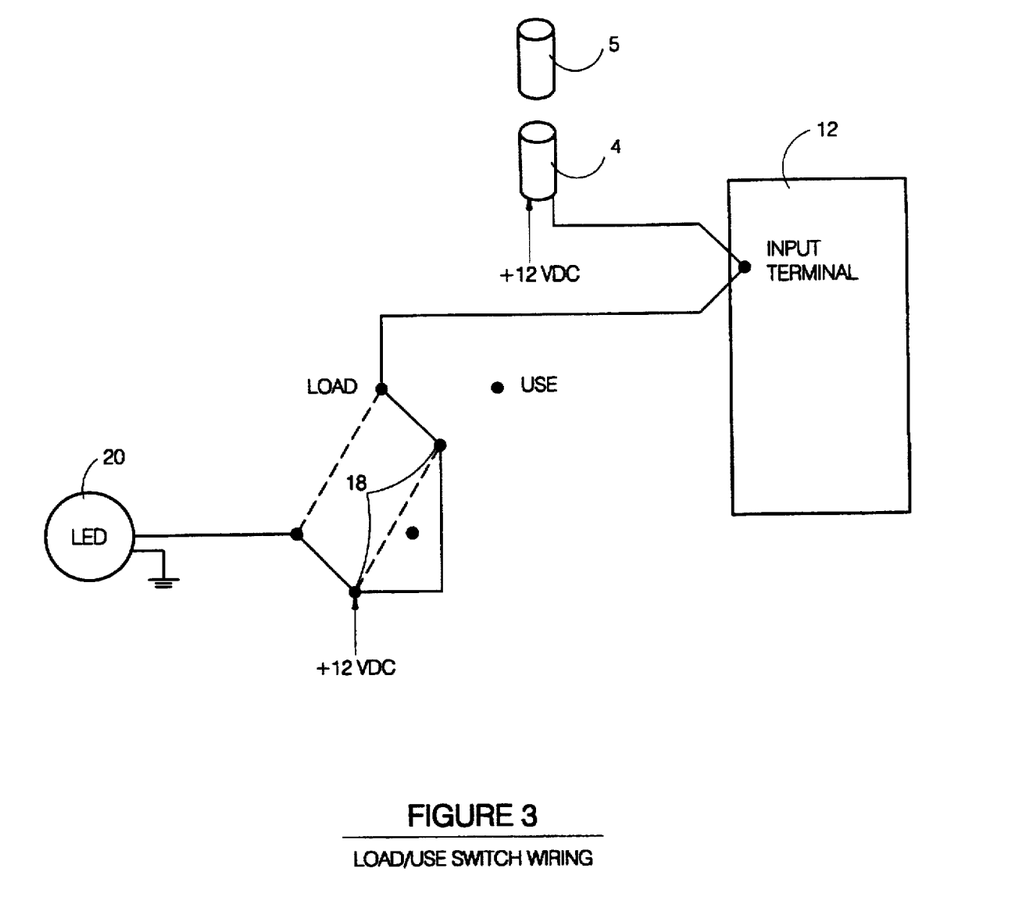
FIG. 3 is a simplified schematic diagram showing how a load/use switch disables monitoring of a subscriber home medication station while the medication container is being loaded with medication.
Figure 4:
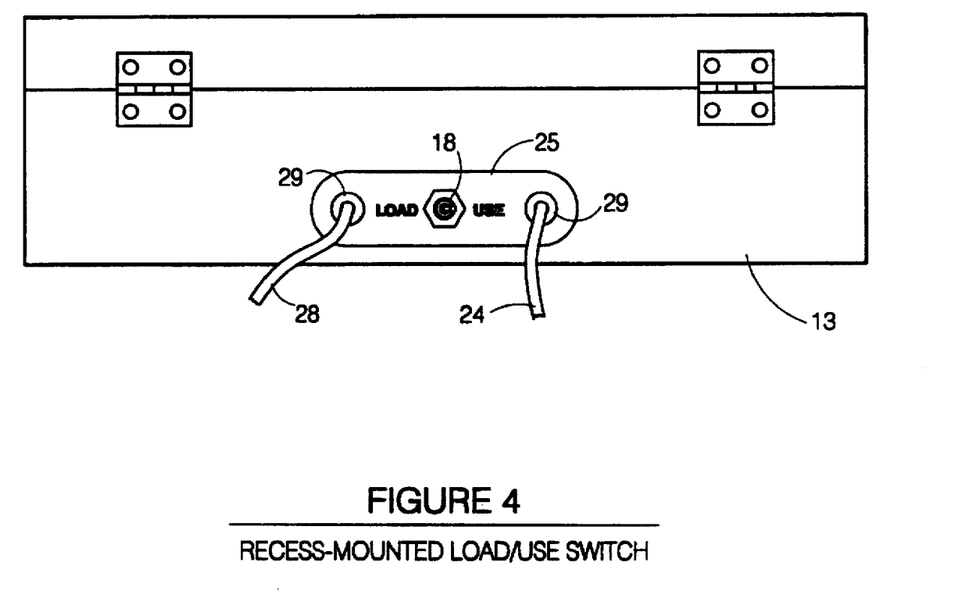
FIG. 4 shows a suggested recessed mounting method for the load/use switch of FIG. 3.

FIG. 3 illustrates the interconnection of DPDT load/use switch 18 with LED indicator 20, digital communicator 12, and lid switch 4 in the preferred embodiment. In alternative embodiments, programmable timer module 14 will be similarly prevented from sensing the opening of box 13 when load/use switch 18 is in "Load" position. FIG. 4, a rear view of box 13, shows a recommended recessed mounting method which helps prevent load/use switch 18 from being accidentally bumped. A small switch mounting panel 25 centers load/use switch 18 in a cutout in box 13's lower back panel. Rubber feed-through grommets 29 on both sides of load/use switch 18 provide entry points for communications cord 28 and DC power cord 24.

Referring again to FIG. 2, optional RF receiver 10's output relay and help-button switch 6 also supply voltage signals to two of digital communicator 12's input points. Help-button 6 is a soft-touch SPST momentary push-button switch. All installed help-button capabilities are always operational, irrespective of position of load/use switch 18. Due to its low cost and ease of implementation, help-button 6 is recommended in all embodiments to provide subscribers with an easy way to manually call for help in event of adverse reaction to medication, or other emergencies. Optional help-button transmitter 8 and RF receiver 10 extend help-button accessibility throughout subscriber homes, and usually into adjacent lawns, gardens, and outbuildings.

All electronic apparatus is powered by an AC adapter 22, which plugs into a wall outlet and converts line voltage to an appropriate DC voltage, 12 VDC is commonly used to power security system apparatus. A DC power cord 24 terminates at a terminal strip 26 for convenience in distributing DC power within the lower cavity. A 2-conductor communications cord 28 is connected to Tip and Ring terminals on digital communicator 12, and is terminated in a standard 1-line modular plug 30. Digital communicator 12 is connected to telephone wiring in a subscriber's home by simply inserting modular plug 30 into an on-site phone jack. A standard Y-connector splitter 32 can be used to allow one phone jack to concurrently accommodate a 1-line house phone and modular plug 30.

In the preferred embodiment, all dosage schedule compliance time checks are performed at the central station. Although such time check programs are not difficult to develop, standard computer techniques designed to monitor the opening and closing of businesses are typically easily adapted to implement this invention's dosage time window monitoring methodology. In security applications, many owners and managers want to be sure that their establishments are opened for business within a prescribed time window on the morning of every business day. They similarly want to be sure that closing occurs within a prescribed evening time window. Dispatchers are alerted if an opening signal isn't received within the morning opening time window, if a closing signal isn't received within the evening closing window, and if opening or closing signals are received at improper times. The ability to monitor multiple open/close time windows of varying widths is commonly provided.

Figure 6:
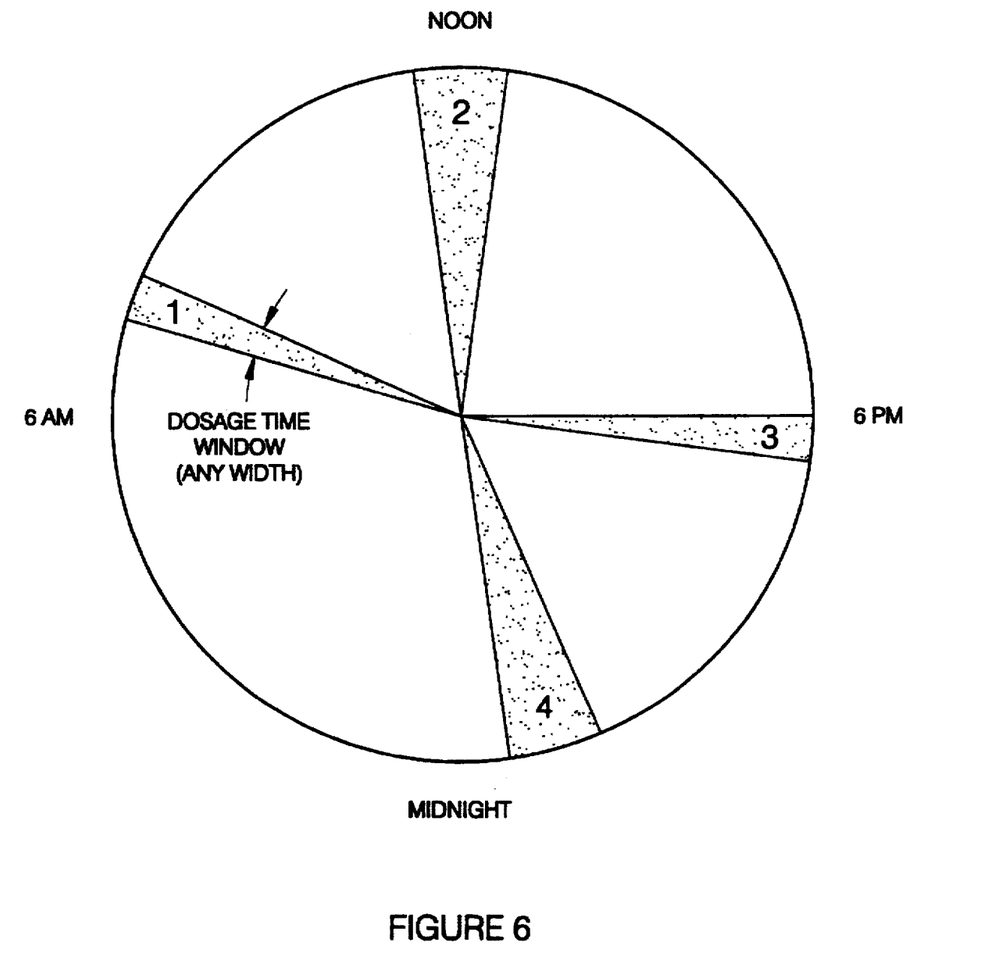
FIG. 6 illustrates the concept of dosage time windows utilized in the monitoring methodology employed for all embodiments.

As commonly done for business openings and closings, definition of subscriber-unique dosage time windows is hence part of the subscriber database record creation process at the central station. FIG. 6 illustrates a typical daily dosage schedule consisting of four dosage time windows, which can be of the same or varying width. Dosage timing and width (time tolerance) for time windows is ideally established by each subscriber's physician.

Performance of all dosage time checks at the central station minimizes cost and complexity of in-home equipment, and implicitly provides frequent verification of digital communicator 12's operational status. Central station communications processing overload could occur, however, if large numbers of subscribers are served. Phone call costs could also be a consideration, where central stations do not offer the economy of 800 numbers for receipt of encoded message transmissions.

Figure 5:
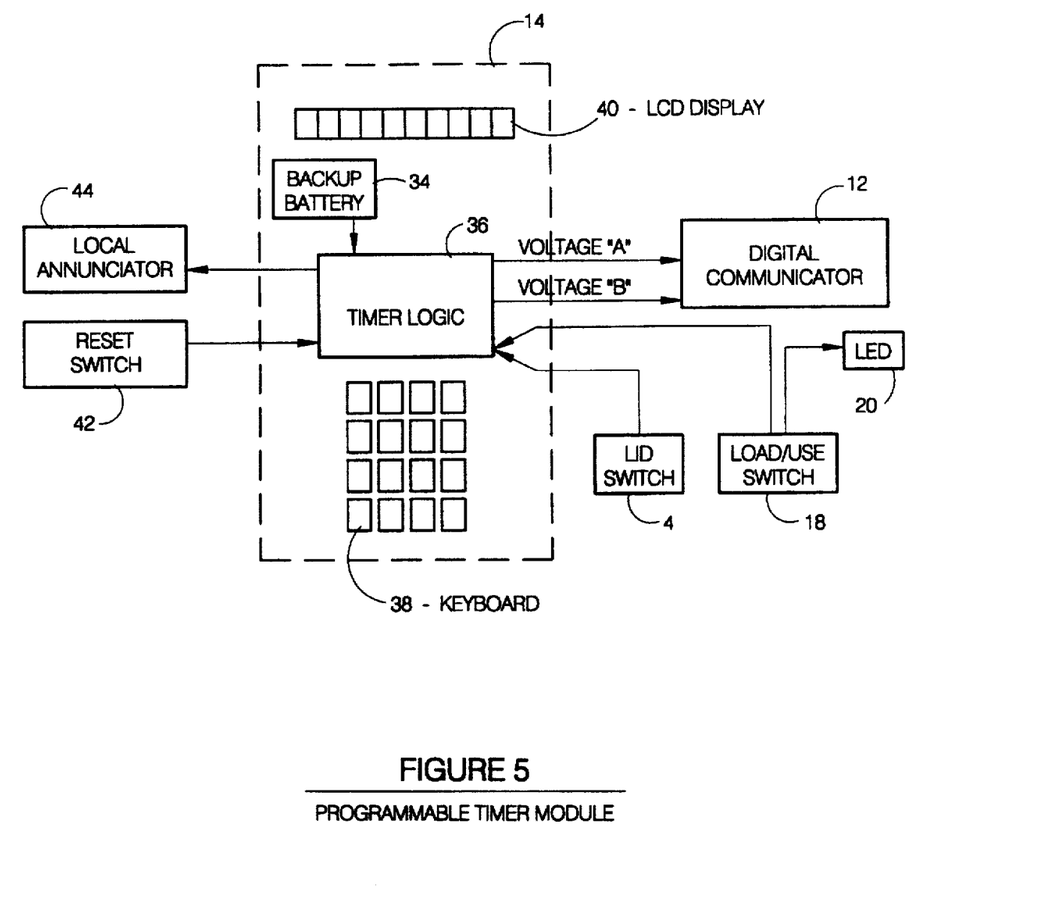
FIG. 5 is a block diagram of the programmable timer module used in both alternative subscriber home medication station embodiments "A" and "B"

Accordingly, two alternative embodiments incorporate all dosage time check functions into a custom-built programmable timer module 14 mounted within box 13. FIG. 5 provides a functional block diagram showing programmable timer module 14's major elements. In the alternative embodiments, automated encoded messages are sent to the central station only in event of detection of a dosage schedule error by timer module 14, or for periodic verification of the home medication station's operational status.

DESCRIPTION OF ALTERNATIVE EMBODIMENTS

Two alternative embodiments functionally differ from the previously described preferred embodiment only in regard to incorporation of a programmable timer module 14, which performs all dosage time check functions. FIG. 5 presents a functional block diagram of programmable timer module 14, comprising timer logic 36, a backup battery 34, a keyboard 38, and a LCD display 40. Keyboard 38 and LCD display 40 are used to set time of day, and start/stop times for dosage time windows as illustrated in FIG. 6. When not in use for making such settings, LCD display 40 could continuously display time of day. Backup battery 34 assures that all time set entries will not be lost in event of AC power failure at the monitored site.

When load/use switch 18 is in "Use" position, timer logic 36 senses lid switch 4's contact closure signals when box 13 is opened and closed during removal of a dosage of medication. Load/use switch 18 parallels lid switch 4's input to timer logic 36, so that timer logic 36 will not be able to sense opening and closing signals from lid switch 4 when load/use switch 18 is put into "Load" position during the loading of medication. As previously described for the preferred embodiment, load/use LED indicator 20 flashes when load/use switch 18 is in "Load" position.

Timer logic 36 is provided with the ability to detect dosage schedule errors which include the following:

Box 13 is not opened within a scheduled dosage time window.

Box 13 is opened between and not within scheduled dosage time windows.

Box 13 is opened within a scheduled dosage time window, and remains open after that time window closes.

Upon detection of a dosage schedule error, timer logic 36 initiates a local annunciator mode for a preset time before transmitting an alarm message to the central station. The preset time is adjustable by alarm type. A piezo beeper and flashing LED are recommended for use in local annunciator 44, providing both audible and visual annunciation to alert the subscriber that an alarm message is about to be transmitted to the central station. If the subscriber opens box 13 before the annunciator mode times out, the alarm condition is canceled.

If box 13 is not opened before the local annunciator mode times out, timer logic 36 outputs an alarm voltage signal "A" to one of digital communicator 12's input points. Digital communicator 12 then responsively transmits an encoded medication alarm message over the communications link to the central station, alerting dispatchers to take appropriate action.

Since alternative embodiments report to the central station on an exception basis, it is essential to periodically verify proper operation of the home medication terminal's electronic apparatus. Referring to FIG. 5, timer logic 36 is provided with the ability to output dosage compliance confirmation voltage signals "B" to another of digital communicator 12's input points. Upon receipt of a dosage compliance confirmation signal "B", digital communicator 12 responsively transmits an encoded dosage compliance confirmation message over communications link 3 to the central station.

Timer logic 36 is programmable to automatically initiate transmission of dosage schedule compliance verification messages at prescheduled time intervals. Such transmissions of course verify proper operation of in-home apparatus, as well as subscriber dosage schedule compliance. Maximum subscriber protection would be provided by initiation of transmission of such messages after each properly executed dosage removal. But that would of course involve as much phone traffic at the central station as required for the preferred embodiment.

In most cases, a reasonable tradeoff between subscriber protection and communications cost can be achieved by transmitting a daily dosage compliance message after each day's last dosage has been successfully accessed within its scheduled time window. The central station monitoring computer is programmed to monitor for receipt of each subscriber's dosage compliance verification messages per daily schedule, and to alert dispatchers to take appropriate action if any such signal is not properly received.

A dosage "alarm-clock" reminder option is also provided to alert subscribers each time a dosage of medication is due. When this feature is activated at subscriber option, timer logic outputs a voltage signal to drive local annunciator 44 at the beginning or midpoint of each scheduled dosage time window. A reset switch 42, identical to lid switch 4, automatically resets local annunciator functions when box 13 is opened.

Figure 7:
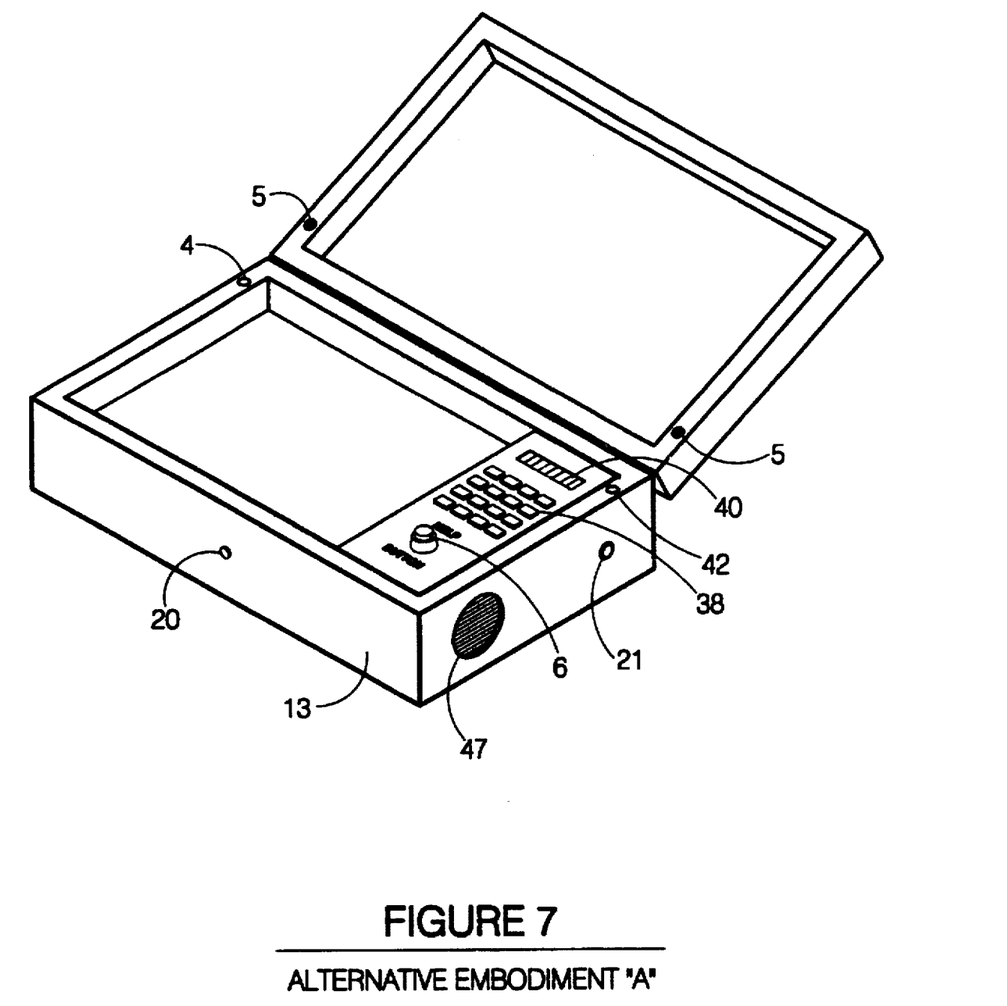
FIG. 7 presents an isometric view of subscriber home medication station alternative embodiment "A", which incorporates a built-in LCD display and keyboard in addition to a programmable timer module.

FIG. 7 illustrates a deluxe alternative embodiment "A", where keyboard 38 and LCD display 40 are built into the home medication station. This embodiment offers the benefit of programming convenience, for appropriate subscribers. For other subscribers, however, it may be preferable to deny easy access to programming features.

Accordingly, alternative embodiment "B" would be similar in appearance to alternative embodiment "A", but would not have integrally mounted keyboard 38 and LCD display 40. In addition to limiting access to programming features, this embodiment would be less expensive than alternative embodiment "A".

Figure 8:
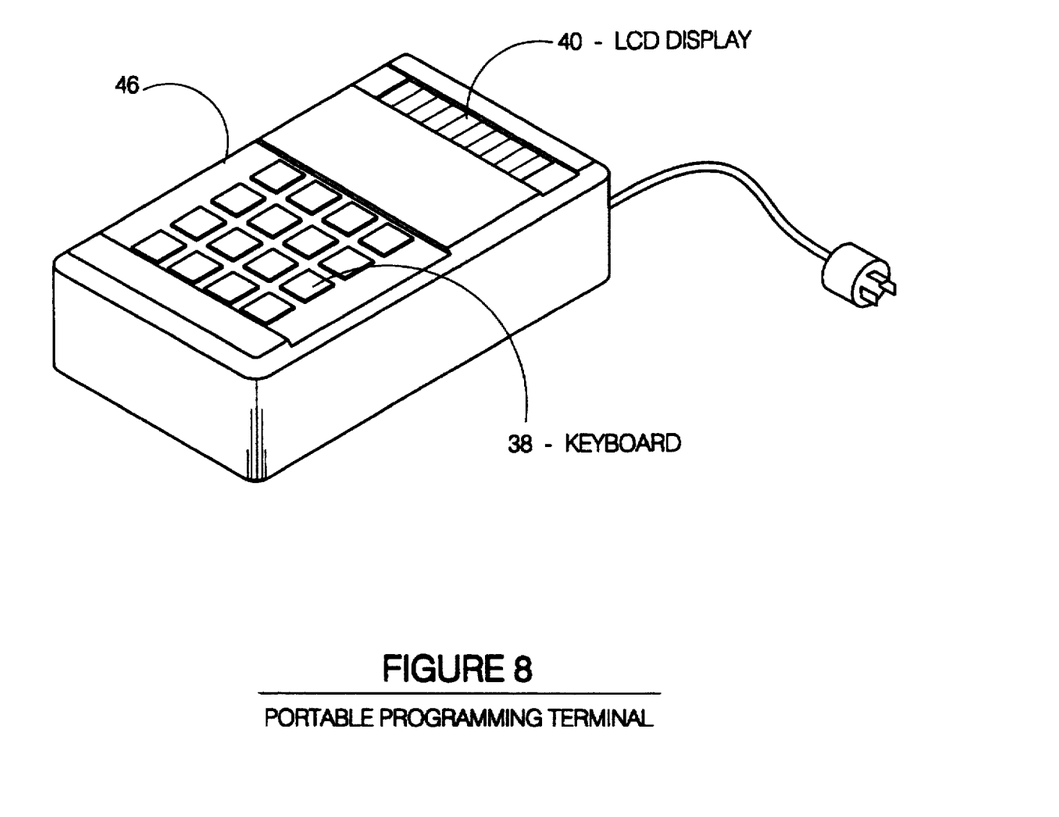
FIG. 8 presents the general appearance of a portable programming terminal which can be plug-connected to medication container alternative embodiment "B."

FIG. 8 conceptually illustrates a compact portable programming terminal 46 comprising LCD display 40 and keyboard 38, which can be plugged into alternative embodiment "B" when required. Referring to FIG. 4, a jack to accommodate plug connection with portable programmer 46 could be mounted in switch mounting panel 25.

Operation—FIGS. 2, 5, 6

A discussion of operation of this invention properly begins with programming which precedes installation of a home medication station at a subscriber's home. Referring to FIG. 2, in all embodiments a digital communicator 12 must be programmed to properly communicate with the central station. The programming process basically loads a few customizing parameter entries into non-volatile memory.

Customizing parameters are typically entered into digital communicator 12 by plugging modular plug 30 into either a special programming terminal or a modem port in a PC loaded with special programming software. Digital communicator manufacturers provide such terminals and PC software, along with simple "cookbook" procedures which facilitate entry of customizing parameters, such as primary and backup central station phone numbers, phone number at the subscriber's home, account number assigned to the subscriber, message format selection, and a range of parameters which customize processing for each input point.

In all embodiments, an account database record must also be created at the central station prior to commencement of monitoring. Central stations which monitor security systems have database structures readily adaptable to the monitoring of self-medication activities. Standard database fields include subscriber name, address, and phone number, names and phone numbers of designated responders, and phone numbers for cognizant police, fire department, ambulance service, family physician, and hospital of choice. Provisions are also typically made to allow entry of medical history which paramedics might find invaluable, if called to respond to a medical emergency.

In the preferred embodiment, dosage time windows are also predefined at the central station as part of the database record creation process. In alternative embodiments, dosage time windows are predefined at the home medication station via keyboard 38 and LCD display 40, as illustrated in FIG. 5. FIG. 6 illustrates a typical daily dosage schedule consisting of four dosage time windows. The monitoring methodology is based on the assumption that dosage schedule compliance can be monitored by assuring that the home medication station is consistently accessed for medication within all scheduled dosage time windows, and at no other times. Each dosage time window is uniquely defined by a start time and a stop time, time window widths can either vary or be the same.

Once preliminary programming has been accomplished, installation at a subscriber's home can be made in a matter of minutes. Referring to FIG. 2, the ornamental box 13 is first placed in a location of choice, with lid closed and load/use switch 18 in "Use" position. Connection to telephone wiring and electric power is then made by simply plugging modular plug 30 into a standard phone jack, and plugging AC adapter 22 into a wall outlet. A phone call is then made to the central station to notify dispatcher staff that a new installation is about to be tested.

Next, load/use switch 18 is put into "Load" position, and it is visually confirmed that load/use LED indicator 20 responsively commences flashing. The lid of box 13 is then opened. If an optional multi-compartment pill dispenser 16 is being used, it is removed, loaded with medication, and put back into box 13's upper cavity. Alternatively, other forms of medication more appropriate for the subscriber are loaded into box 13's upper cavity, such as medicine bottles, pill bottles, etc. Box 13's lid is then closed, and it is visually confirmed that load/use LED indicator 20 responsively stops flashing when load/use switch 18 is returned to "Use" position.

Data communications testing is next quickly accomplished by opening the lid of box 13, pressing help-button switch 6, and then closing the lid of box 13. If present, optional miniature RF wireless transmitter 8's help-button is also pressed before, after, or during the opening and closing of box 13's lid. If optional 2-way audio module 17 is installed, the ability to enter into 2-way conversation with a central station dispatcher is also confirmed. A dispatcher is then asked to verify that proper encoded messages were received, either during 2-way audio testing or via a phone call to the central station.

Operating procedures during normal use are quite simple. Referring to FIG. 2, lid switch 4 is actuated when box 13 is opened and closed during removal of each dosage of medication. In the preferred embodiment, switch 4's contact closure signals cause digital communicator 12 to responsively transmit an encoded opening message as box 13's lid is opened, and an encoded closing message when the lid closes. The central station receives and decodes the messages, and automatically verifies that lid switch 4 is being actuated within one of the subscriber's uniquely scheduled dosage time windows.

FIG. 6 illustrates a predefined dosage schedule consisting of four daily dosages of medication. Each subscriber can have uniquely scheduled dosage time windows, and each time window can have the same or a unique width (time tolerance). Dispatchers are promptly alerted to take appropriate action upon detection of the following types of discrepancies:

a. An opening signal is not received within a scheduled time window.

b. An opening signal is received between and not within time windows.

c. An opening signal is received within a scheduled time window, but a closing signal is not.

Applied to the monitoring of self-medication, discrepancy "a" signals that a scheduled dosage has been forgotten, the most common self-medication error. A dispatcher phone call can remind the subscriber to take the missed dosage before much time elapses. Discrepancy "b" may mean that a dosage is about to be taken at the wrong time. Prompt dispatcher phone follow-up may prevent an off-schedule dosage from being taken. At minimum, the system will have provided early warning to be prepared to counter any adverse effects an off-schedule dosage might produce. Discrepancy "c" could be due to a number of causes, ranging from subscriber forgetfulness to a heart attack. Whatever the discrepancy, a prompt dispatcher phone call to the subscriber's home will be made. If the subscriber can't be reached by phone, a responder will quickly be dispatched to the subscriber's home.

Referring to FIG. 5, in alternative embodiments, lid switch 4's opening and closing signals are sensed by timer logic 36, which performs all dosage time checks. Detection of any of the previously described types of discrepancies causes timer logic 36 to activate local annunciator 44 for a preset time before initiating transmission of an alarm message to the central station. The alarm condition is canceled if lid switch 4 is actuated before the local annunciator mode times out. Otherwise, timer logic 36 outputs a voltage signal "A" to digital communicator 12, which responsively transmits an encoded dosage schedule error signal to the central station.

Timer logic 36 is also programmable to automatically initiate periodic transmission of dosage compliance verification messages. Such messages confirm that subscriber medication dosage schedule compliance is being maintained, and also periodically verify proper operation of home medication station electronic apparatus. It is recommended that one daily dosage compliance message should be transmitted after the last dosage of the day has been successfully accessed within its scheduled time window. Message transmission is initiated when timer logic 36 outputs a voltage signal "B" to digital communicator 12, which responsively transmits an encoded dosage compliance verification message to the central station. Per standard security system practice, the central station monitoring computer is programmed to monitor for receipt of dosage compliance verification messages per the chosen schedule, and to alert dispatchers to take appropriate action if any such signal is not properly received. Referring again to FIG. 2, in all embodiments of this invention subscribers may utilize help-button switch 6 and optional help-button transmitter 8 (if present) to cause digital communicator 12 to responsively transmit encoded messages summoning aid in event of an adverse reaction to medication, or other emergency. In the more serious emergencies, however, subscribers are often incapable of pressing a help-button. Every year thousands of senior citizens lose their lives at home simply because nobody knows that they need help, some lie helpless for days.

As a valuable "side-benefit", all embodiments of this invention prevents the occurrence of such scenarios. It is readily apparent that the longest time a subscriber emergency might go undetected is the maximum time between consecutively scheduled dosages. Central station dispatchers will follow-up promptly the first time a scheduled dosage is missed, for whatever reason.

SUMMARY, RAMIFICATIONS, AND SCOPE

Accordingly, the reader will see that this invention provides a reliable in-home self-medication apparatus and method for remote monitoring which will maximize compliance with prescribed dosage schedules. It concurrently assures that adverse reactions to medication or other emergencies which render a subscriber helpless cannot go undetected longer than the maximum time between consecutively scheduled dosages of medication. These combined capabilities offer a welcome extension of the duration of an independent lifestyle for a great many of the elderly and infirm. Furthermore, this invention offers additional advantages in that

- it provides early detection of forgotten dosages and off-schedule accessing of medication, so that adverse effects of such errors can be minimized;
- its simple design permits a low overall cost, making the apparatus and monitoring affordable for large numbers of elderly subscribers;
- its design is easy to use, non-intimidating, and non-demeaning for elderly subscribers;
- its monitoring methodology permits subscribers the latitude to take medication within time windows of specifiable width, as opposed to requiring that medication be taken at specific times;
- its design inherently provides frequent verification of proper operation of in-home communicator electronics;
- it provides subscribers with effective means to alert a central monitoring center if help is needed in event of an adverse reaction to medication.

Although the preceding description contains many specificities, these should not be construed as limiting the scope of the invention but as merely providing illustrations of some of the presently preferred embodiments of this invention. For example, a variety of container designs could be used, including wall-mounted containers, containers having other shapes, containers built into nightstands or other furniture, containers sharing cabinetry which houses other equipment, etc. Also, the functions of the various PC boards itemized in the preceding description might be combined into fewer PC boards or one PC board, different types of electrical switches could be used, etc.

Thus the scope of the invention should be determined by the appended claims and their legal equivalents, rather than by the examples given.

I claim:

1. A self-medication monitoring system for monitoring subscriber compliance with uniquely prescribed medication dosage schedules via a communication link, comprising:
    - a subscriber remote station for transmission of information corresponding to a subscriber's self-medication activities via said communication link, said subscriber remote station further comprising:
        - a switch means operative to generate predetermined signals corresponding to a subscriber's self-medication activities in response to said subscriber's self-medication activities; and
        - a communicator means operative to be activated by said generated predetermined signals to responsively transmit corresponding predetermined subscriber self-medication activity messages to the central station via said communications link;
    - a central monitoring station for receiving, via said communication link, and processing the information corresponding to a subscriber's self-medication activities to alarm monitor subscriber compliance with uniquely prescribed medication dosage schedules, said central monitoring station further comprising:
        - a processor means operative at the central station to uniquely preschedule non-overlapping daily medication dosage time windows of the same or varying time width for each subscriber, one such time window for each of a subscriber's prescribed daily dosages, each said time window bounded by a unique opening time and a unique closing time specified by or for said subscriber, wherein said subscriber's compliance with prescribed medication dosage schedules can be inferred if each of said subscriber self-medication activity messages is received at said central station within its respective prescheduled time window; and
        - a processor means operative at said central station to alarm monitor said self-medication activity messages to assure that compliance with the subscriber's prescribed medication dosage schedules is indicated within each of said subscriber's prescheduled time windows, and at no other times.

2. The self-medication monitoring system of claim 1, wherein said remote station is configured as a home medication station for storing said subscriber's prescription medication in a simple container of predetermined shape and volume, said remote station further comprising a storage compartment for storing said prescription medication directly or in package means adapted to meet said subscriber's needs, and lid means operative to be opened by said subscriber to gain access to said medication, wherein said switch means is actuated each time said lid means is opened and closed.

3. The self-medication monitoring system of claim 1, wherein said remote station further includes two-way audio means operative to enable two-way voice communications between said central station and said remote station via said communication link upon occurrence of predetermined alarm conditions.

4. The self-medication monitoring system of claim 1, wherein said remote station further includes a miniature radio receiver which receives RF signals of predetermined frequency from at least one miniature portable wireless help-button RF transmitter, and responsively activates said communicator means to become operative to responsively transmit a predetermined alarm message to said central station via said communication link.

5. The self-medication monitoring system of claim 1, wherein said remote station further includes at least one help-button switch, which when actuated causes said communicator means to become operative to responsively transmit a predetermined alarm message to said central station via said communication link.

6. A self-medication monitoring system for monitoring subscriber noncompliance with uniquely prescribed medication dosage schedules and for transmission of noncompliance information over a communication link to a central monitoring station, comprising:
    - a subscriber remote station for monitoring information indicative of subscriber noncompliance with uniquely prescribed medication dosage schedules and for transmission of noncompliance information via said communication link, said subscriber remote station further comprising:
        - a switch means operative to generate predetermined signals corresponding to a subscriber's self-medication activities in response to said subscriber's self-medication activities;

a programmable timer means operative to uniquely preschedule non-overlapping daily medication dosage time windows of the same or varying time width for any subscriber, one such time window for each of a subscriber's prescribed daily dosages of medication, each said time window bounded by a unique opening time and a unique closing time specified by or for said subscriber, wherein said subscriber's prescribed medication dosage schedule compliance can be inferred if each of said subscriber self-medication activity messages is generated within it's respective prescheduled time window;

a programmable timer means operative to monitor said self-medication activity messages to assure that compliance with the subscriber's prescribed medication dosage schedules is indicated within each of said subscriber's prescheduled time windows, and at no other times, and to responsively output subscriber alert signals upon detection of any indicated non-compliance;

a local annunciator means operative to be activated in response to said subscriber alert signals;

a programmable timer means operative to responsively output alarm signals if said subscriber does not take predetermined action to correct said noncompliance within a predetermined time after activation of said local annunciator means by said alert signals; and a communicator means operative to be activated by said alarm signals to responsively transmit predetermined alarm messages to said central station via said communications link.

7. The self-medication monitoring system of claim 6, wherein said remote station is configured as a home medication station for storing said subscriber's prescription medication in a simple container of predetermined shape and volume, said remote station further comprising a storage compartment and lid means operative to be opened by said subscriber to gain access to said medication, for storing said prescription medication directly or in package means adapted to meet said subscriber's needs, wherein said switch means is actuated each time said lid means is opened and closed.

8. The self-medication monitoring system of claim 6, wherein said remote station further includes two-way audio means operative to enable two-way voice communications between said central station and said remote station via said communication link upon occurrence of predetermined alarm conditions.

9. The self-medication monitoring system of claim 6, wherein said remote station further includes a miniature radio receiver which receives RF signals of predetermined frequency from at least one miniature portable wireless help-button RF transmitter, and responsively activates said communicator means to become operative to responsively transmit a predetermined alarm message to said central station via said communication link.

10. The self-medication monitoring system of claim 6, wherein said remote station further includes at least one help-button switch, which when actuated causes said communicator means to become operative to responsively transmit a predetermined alarm message to said central station via said communication link.

11. A self-medication monitoring method for monitoring subscriber compliance with uniquely prescribed medication dosage schedules via a communication link, comprising the steps of:

a) providing a subscriber a remote station for transmission of information corresponding to a subscriber's self-medication activities via said communication link;

b) operating a switch means at said remote station to generate predetermined signals corresponding to a subscriber's self-medication activities in response to said subscriber's self-medication activities;

c) operating a communicator means at said remote station to be activated by said generated predetermined signals to responsively transmit corresponding predetermined subscriber self-medication activity messages to the central station via said communications link;

d) providing a central monitoring station for receiving, via said communication link, and processing the information corresponding to a subscriber's self-medication activities to alarm monitor subscriber compliance with uniquely prescribed medication dosage schedules;

e) operating a processor means at said central station to uniquely preschedule non-overlapping daily medication dosage time windows of the same or varying time width for each subscriber, one such time window for each of a subscriber's prescribed daily dosages, each said time window bounded by a unique opening time and a unique closing time specified by or for said subscriber, wherein said subscriber's compliance with prescribed medication dosage schedules can be inferred if each of said subscriber self-medication activity messages is received at said central station within its respective prescheduled time window; and f) operating a processor means at said central station to alarm monitor said self-medication activity messages to assure that compliance with the subscriber's prescribed medication dosage schedules is indicated within each of said subscriber's prescheduled time windows, and at no other times.

12. The self-medication monitoring method of claim 11, wherein said step of providing said remote station includes configuring the remote station as a home medication station for storing said subscriber's prescription medication in a simple container of predetermined shape and volume, and providing said remote station with a storage compartment for storing said prescription medication directly or in package means adapted to meet said subscriber's needs, and with a lid operable to be opened by said subscriber to gain access to said medication, and actuating said switch means each time said lid means is opened and closed.

13. The self-medication monitoring method of claim 11, wherein said remote station is further provided a two-way audio means, and operating said audio means to enable two-way voice communications between said central station and said remote station via said communication link upon occurrence of predetermined alarm conditions.

14. The self-medication monitoring method of claim 11, wherein said remote station is further provided a miniature radio receiver to receive RF signals of predetermined frequency from at least one miniature portable wireless help-button RF transmitter, and to responsively activate said communicator means to become operative to responsively transmit a predetermined alarm message to said central station via said communication link.

15. The self-medication monitoring method of claim 11, wherein said remote station is further provided at least one help-button switch, which is selectively actuated to cause said communicator means to become operative to responsively transmit a predetermined alarm message to said central station via said communication link.

* * * * *